United States Patent
Forsell

(10) Patent No.: US 9,278,158 B2
(45) Date of Patent: Mar. 8, 2016

(54) MULTI-MATERIAL INCONTINENCE TREATMENT CONSTRUCTION DEVICE

(76) Inventor: Peter Forsell, Zug (CH)

(*) Notice: Subject to any disclaimer, the term of this patent is extended or adjusted under 35 U.S.C. 154(b) by 0 days.

(21) Appl. No.: 11/889,756

(22) Filed: Aug. 16, 2007

(65) Prior Publication Data

US 2008/0045783 A1 Feb. 21, 2008

Related U.S. Application Data

(63) Continuation of application No. 10/463,873, filed on Jun. 18, 2003, now abandoned.

(60) Provisional application No. 60/398,824, filed on Jul. 29, 2002.

(51) Int. Cl.

| A61F 2/02 | (2006.01) |
|---|---|
| A61L 27/34 | (2006.01) |
| A61L 27/30 | (2006.01) |
| A61L 31/08 | (2006.01) |
| A61L 31/10 | (2006.01) |

(52) U.S. Cl.
CPC ............. *A61L 27/34* (2013.01); *A61L 27/306* (2013.01); *A61L 31/088* (2013.01); *A61L 31/10* (2013.01)

(58) Field of Classification Search
CPC ... A61G 2/0063; A61G 2/0045; A61G 2/042; A61G 2/0009; A61G 2/0036; A61G 2/04; A61G 2/82; A61G 2/02; A61G 2002/0068; A61G 5/005
USPC .............. 600/29–32, 37; 128/885; 606/151; 623/23.64–23.67
See application file for complete search history.

(56) References Cited

U.S. PATENT DOCUMENTS

| 2,060,913 A | 11/1936 | Weaver |
| 2,795,641 A | 6/1957 | Rowell |
| 3,209,081 A | 9/1965 | Ducote et al. |
| 3,366,975 A | 2/1968 | Pangman |
| 3,731,679 A | 5/1973 | Wilhelmson et al. |
| 3,750,194 A | 8/1973 | Summers |
| 3,817,237 A | 6/1974 | Bolduc |
| 3,855,122 A | 12/1974 | Bourganel |
| 3,875,928 A | 4/1975 | Angelchik |

(Continued)

FOREIGN PATENT DOCUMENTS

| DE | 19511998 | 10/1996 |
| DE | 20004915 | 8/2001 |

(Continued)

OTHER PUBLICATIONS

Publication No. EP 1568338A2, dated Aug. 31, 2005, for European Patent Application No. 05010107.0.

(Continued)

*Primary Examiner* — Christine H Matthews

(57) ABSTRACT

An implantable constriction device for treating an incontinent patient comprises an elongate composite structure adapted to constrict the urethra, urine bladder, anus, colon or rectum of the patient. The elongate composite structure is composed of a base material, such as hard silicone, making the composite structure self-supporting. Property improving material is provided for improving at least one physical property of the composite structure other than self-supporting properties, such as fatigue resistance, liquid impermeability, aggressive body cells resistance, anti-friction properties and lifetime.

12 Claims, 2 Drawing Sheets

(56) References Cited

U.S. PATENT DOCUMENTS

| | | |
|---|---|---|
| 3,954,102 A | 5/1976 | Buuck |
| 4,009,711 A | 3/1977 | Uson |
| 4,026,305 A | 5/1977 | Brownlee et al. |
| 4,201,202 A | 5/1980 | Finney et al. |
| 4,235,222 A | 11/1980 | Ionescu |
| 4,243,306 A | 1/1981 | Bonini |
| 4,246,893 A | 1/1981 | Berson |
| 4,298,998 A | 11/1981 | Naficy |
| 4,318,396 A | 3/1982 | Finney |
| 4,342,308 A | 8/1982 | Trick |
| 4,369,771 A | 1/1983 | Trick |
| 4,412,530 A | 11/1983 | Burton |
| 4,424,807 A | 1/1984 | Evans |
| 4,428,365 A | 1/1984 | Hakky |
| 4,480,642 A | 11/1984 | Stoy et al. |
| 4,517,967 A | 5/1985 | Timm et al. |
| 4,542,753 A | 9/1985 | Brenman et al. |
| 4,550,720 A | 11/1985 | Trick |
| 4,556,050 A * | 12/1985 | Hodgson et al. ............... 600/30 |
| 4,559,930 A | 12/1985 | Cobiski |
| 4,592,339 A * | 6/1986 | Kuzmak et al. ............... 128/899 |
| 4,592,355 A | 6/1986 | Antebi |
| 4,602,621 A | 7/1986 | Hakky |
| 4,664,100 A | 5/1987 | Rudloff |
| 4,679,560 A | 7/1987 | Galbraith |
| 4,696,288 A | 9/1987 | Kuzmak et al. |
| 4,711,231 A | 12/1987 | Finegold et al. |
| 4,723,538 A | 2/1988 | Stewart et al. |
| 4,756,949 A | 7/1988 | Spence et al. |
| 4,771,780 A | 9/1988 | Sholder |
| 4,820,302 A | 4/1989 | Woodroof |
| 4,828,544 A | 5/1989 | Lane et al. |
| 4,828,990 A | 5/1989 | Higashi et al. |
| 4,829,990 A | 5/1989 | Thuroff et al. |
| 4,846,794 A | 7/1989 | Hertzer |
| 4,941,461 A | 7/1990 | Fischell |
| 4,942,668 A | 7/1990 | Franklin |
| 4,955,907 A | 9/1990 | Ledergerber |
| 4,958,630 A | 9/1990 | Rosenbluth et al. |
| 4,982,731 A | 1/1991 | Lue et al. |
| 5,012,822 A | 5/1991 | Schwarz |
| 5,042,084 A | 8/1991 | Daly |
| 5,062,416 A | 11/1991 | Stucks |
| 5,067,491 A | 11/1991 | Taylor et al. |
| 5,074,868 A | 12/1991 | Kuzmak |
| 5,160,338 A | 11/1992 | Vincent |
| 5,226,429 A | 7/1993 | Kuzmak |
| 5,304,206 A | 4/1994 | Baker, Jr. et al. |
| 5,437,605 A | 8/1995 | Helmy |
| 5,449,368 A | 9/1995 | Kuzmak |
| 5,453,079 A | 9/1995 | Schwaninger |
| 5,454,840 A | 10/1995 | Krakovsky et al. |
| 5,509,888 A | 4/1996 | Miller |
| 5,518,504 A | 5/1996 | Polyak |
| 5,540,731 A | 7/1996 | Testerman |
| 5,578,069 A | 11/1996 | Miner, II |
| 5,601,604 A | 2/1997 | Vincent |
| 5,704,893 A | 1/1998 | Timm |
| 5,749,909 A | 5/1998 | Schroeppel et al. |
| 5,769,877 A | 6/1998 | Barreras |
| 5,771,903 A | 6/1998 | Jakobsson |
| 5,772,903 A | 6/1998 | Hirsch |
| 5,823,991 A | 10/1998 | Shim |
| 5,855,613 A | 1/1999 | Antanavich et al. |
| 5,873,904 A | 2/1999 | Ragheb et al. |
| 5,900,909 A | 5/1999 | Parulski et al. |
| 5,910,149 A | 6/1999 | Kuzmak |
| 5,938,584 A | 8/1999 | Ardito et al. |
| 5,938,669 A | 8/1999 | Klaiber et al. |
| 5,978,712 A | 11/1999 | Suda et al. |
| 6,042,608 A | 3/2000 | Ishikawa et al. |
| 6,067,991 A | 5/2000 | Forsell |
| 6,074,341 A * | 6/2000 | Anderson et al. ............... 600/29 |
| 6,102,922 A | 8/2000 | Jakobsson et al. |
| 6,117,067 A | 9/2000 | Gil-Vernet |
| 6,135,945 A | 10/2000 | Sultan |
| 6,162,238 A | 12/2000 | Kaplan et al. |
| 6,185,452 B1 | 2/2001 | Schulman et al. |
| 6,210,347 B1 | 4/2001 | Forsell |
| 6,221,060 B1 | 4/2001 | Willard |
| 6,287,315 B1 | 9/2001 | Wijeratne et al. |
| 6,319,191 B1 | 11/2001 | Sayet et al. |
| 6,372,244 B1 | 4/2002 | Antanavich et al. |
| 6,436,054 B1 | 8/2002 | Viola et al. |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,503,189 B1 | 1/2003 | Forsell |
| 6,558,315 B1 * | 5/2003 | Kuyava ............... 600/40 |
| 6,638,208 B1 | 10/2003 | Natarajan et al. |
| 6,709,385 B2 | 3/2004 | Forsell |
| 6,895,280 B2 | 5/2005 | Meadows et al. |
| 6,915,165 B2 | 7/2005 | Forsell |
| 6,953,429 B2 | 10/2005 | Forsell |
| 7,011,624 B2 | 3/2006 | Forsell |
| 7,017,583 B2 | 3/2006 | Forsell |
| 7,207,936 B2 | 4/2007 | Forsell |
| 7,235,044 B2 | 6/2007 | Forsell |
| 7,250,037 B2 | 7/2007 | Shermer et al. |
| 7,338,437 B2 | 3/2008 | Forsell |
| 7,367,938 B2 | 5/2008 | Forsell |
| 7,371,208 B2 | 5/2008 | Forsell |
| 7,407,479 B2 | 8/2008 | Forsell |
| 7,407,481 B2 | 8/2008 | Forsell |
| 7,442,165 B2 | 10/2008 | Forsell |
| 7,621,863 B2 | 11/2009 | Forsell |
| 7,648,455 B2 | 1/2010 | Forsell |
| 7,666,132 B2 | 2/2010 | Forsell |
| 2001/0011543 A1 | 8/2001 | Forsell |
| 2002/0091395 A1 | 7/2002 | Gabbay |
| 2002/0099438 A1 | 7/2002 | Furst |
| 2002/0133225 A1 | 9/2002 | Gordon |
| 2002/0182392 A1 | 12/2002 | Welch, Jr. et al. |
| 2002/0183588 A1 * | 12/2002 | Fierro ............... 600/30 |
| 2003/0009221 A1 | 1/2003 | Forsell |
| 2003/0032857 A1 | 2/2003 | Forsell |
| 2003/0036803 A1 | 2/2003 | McGhan |
| 2003/0060893 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093141 A1 | 5/2003 | Dimatteo et al. |
| 2003/0100929 A1 | 5/2003 | Forsell |
| 2003/0105385 A1 | 6/2003 | Forsell |
| 2003/0109771 A1 | 6/2003 | Forsell |
| 2003/0125605 A1 | 7/2003 | Forsell |
| 2003/0125768 A1 | 7/2003 | Peter |
| 2004/0034275 A1 | 2/2004 | Forsell |
| 2004/0133219 A1 | 7/2004 | Forsell |
| 2004/0177918 A1 | 9/2004 | Murata et al. |
| 2006/0094926 A1 | 5/2006 | Forsell |
| 2006/0111791 A1 | 5/2006 | Forsell |
| 2006/0142635 A1 | 6/2006 | Forsell |
| 2006/0149124 A1 | 7/2006 | Forsell |
| 2006/0149125 A1 | 7/2006 | Forsell |
| 2006/0167337 A1 | 7/2006 | Forsell |
| 2006/0235482 A1 | 10/2006 | Forsell |
| 2007/0015959 A1 | 1/2007 | Forsell |
| 2007/0073099 A1 | 3/2007 | Forsell |
| 2007/0232848 A1 | 10/2007 | Forsell |
| 2008/0045783 A1 | 2/2008 | Forsell |

(56) References Cited

U.S. PATENT DOCUMENTS

| | | |
|---|---|---|
| 2008/0200753 A1 | 8/2008 | Forsell |
| 2008/0275296 A1 | 11/2008 | Forsell |
| 2009/0018388 A1 | 1/2009 | Forsell |
| 2009/0054725 A1 | 2/2009 | Forsell |
| 2009/0240100 A1 | 9/2009 | Forsell |
| 2009/0250068 A1 | 10/2009 | Forsell |
| 2010/0145138 A1 | 6/2010 | Forsell |
| 2010/0145139 A1 | 6/2010 | Forsell |
| 2010/0217067 A1 | 8/2010 | Forsell |

FOREIGN PATENT DOCUMENTS

| | | |
|---|---|---|
| EP | 0200286 | 11/1986 |
| EP | 0626154 A1 | 11/1994 |
| EP | 0679373 | 11/1995 |
| EP | 0747069 | 12/1996 |
| EP | 1072238 | 1/2001 |
| EP | 0716834 | 8/2001 |
| FR | 2688693 | 9/1993 |
| FR | 2692777 | 12/1993 |
| FR | 2717069 | 9/1995 |
| FR | 27565485 | 6/1998 |
| FR | 2797181 | 2/2001 |
| SU | 906-526 | 2/1982 |
| WO | 94/27504 | 12/1994 |
| WO | 96/01597 | 1/1996 |
| WO | 96/11036 | 4/1996 |
| WO | 97/41799 | 11/1997 |
| WO | 00/09048 | 2/2000 |
| WO | 00/15158 | 3/2000 |
| WO | 0112078 | 2/2001 |
| WO | 01/47431 | 7/2001 |
| WO | 0147434 | 7/2001 |
| WO | 0147435 | 7/2001 |
| WO | 0167996 | 9/2001 |
| WO | 2004/012806 | 2/2004 |

OTHER PUBLICATIONS

"NPC-102 N Medical Angioplasty Sensor" web page at www.novas-sensor.com/catalog/NPC_102.html.
Webster's II New River side University, 1984, pp. 573,1000.
Database WPI; Week 1999629; Derwenr Publications Ltd., London GB; Class A96; AN 1996-279360.
U.S. Appl. No. 11/988,450, Forsell.
U.S. Appl. No. 12/839,115; Forsell.
U.S. Appl. No. 12/839,162; Forsell.
U.S. Appl. No. 12/859,454; Forsell.
U.S. Appl. No. 09/373,224; Forsell.

* cited by examiner

MULTI-MATERIAL INCONTINENCE TREATMENT CONSTRUCTION DEVICE

This application is a continuation of application Ser. No. 10/463,873, filed Jun. 18, 2003, which claims the benefit of Provisional Application No. 60/398,824, filed Jul. 29, 2002, the entire contents of which are hereby incorporated by reference in this application.

BACKGROUND OF THE INVENTION

The present invention relates to an implantable constriction device for constricting the urethra, urine bladder, anus, colon or rectum of an incontinent patient.

This kind of constriction device, in the form of a banding device in which a band encircles and adjustably constricts a portion of a patient's urethra, urine bladder, anus, colon or rectum, has been used in surgery for treating anal and urinary incontinence. In practice, the band is made of silicone, which is a material approved and widely used for implantation. Moreover, the silicone band has an acceptable tensile strength and is fairly resistant to aggressive body fluids. Where the band is hydraulically adjusted, the hydraulic fluid used typically is an isotonic salt solution mixed with other conventional materials.

A problem with traditional silicone bands, however, is that the silicone material gives the band certain inadequate properties, such as poor fatigue resistance and poor endurance of static bending forces, which over time might result in breakage of the band. Furthermore, silicone is a material that is semi-permeable by liquid, which is a drawback to hydraulic silicone bands, because hydraulic fluid can escape by diffusing through the silicone material. As a result, accurate adjustments of a hydraulic band are difficult to perform because of the loss of hydraulic fluid and the need for the patient to regularly visit a doctor to add hydraulic fluid to and calibrate the constriction device. These inadequate properties are serious, considering that the band is implanted for the rest of the patient's life. Another problem is that the band somewhat restrains the dynamic movements of adjacent organs necessary for the transportation of urine or fecal matter. As a consequence, the band might erode, and over time injure the urethra, urine bladder, anus, colon or rectum.

SUMMARY OF THE INVENTION

The object of the present invention is to provide a new implantable constriction device for treating urinary and anal incontinence having improved properties as compared to traditional constriction devices.

Accordingly, the present invention provides an implantable constriction device for treating an incontinent patient, the device comprising an elongate composite structure adapted to constrict the urethra, urine bladder, anus, colon or rectum of the patient, wherein the elongate composite structure is composed of a base material making the composite structure self-supporting and property improving means for improving at least one physical property of the composite structure other than self-supporting properties.

In accordance with a first embodiment of the invention, the property improving means comprises a coating on the base material at least along a side of the elongate composite structure that is intended to contact the urethra, urine bladder, anus, colon or rectum, wherein the coating has better aggressive body fluid resistance than the base material. Such a coating may comprise a Teflon™, i.e., PTFE or poly-tetra-flouro-ethylene, or Parylene™, i.e., poly-paraxylylene polymer, coating, or a biocompatible metal coating, such as gold, silver or titanium. As a result, the constriction device can be protected from damaging influences of aggressive body fluids, possibly for the rest of the patient's life.

Where traditional silicone material constitutes the base material, a Teflon™, i.e., PTFE or poly-tetra-flouro-ethylene, or Parylene™, i.e., poly-paraxylylene polymer, coating also provides the composite structure with better anti-friction properties than the base material. Good anti-friction properties of the composite structure reduce the risk of the elongate composite structure eroding the urethra, urine bladder, anus, colon or rectum. This is proven by tests, in which the surface of traditional silicone bands has been polished before use. Accordingly, the test results indicate significant improvements in avoiding erosion of the urethra, urine bladder, anus, colon or rectum.

Furthermore, the Teflon™, i.e., PTFE or poly-tetra-flouro-ethylene, Parylene™, i.e. poly-paraxylylene polymer, or metal coating also makes the composite structure, in which the base material is made of silicone, stronger than the traditional silicone band. A stronger band reduces the risk of fracture.

In one alternative to the first embodiment, the elongate composite structure is designed for mechanical adjustment, such as the mechanical solutions disclosed in International Application No. WO 01/45486. In this alternative, the property improving means comprises a core of a soft viscoelastic material, such as silicone gel, typically having a hardness less than 20 Shure, cellulose gel or collagen gel. Where silicone gel is chosen, it may be "Med 3-6300" manufactured by Nusil. Hard silicone constitutes the base material, typically having a hardness of at least 60 Shure, and covers the soft core of viscoelastic material. The soft core makes the implanted elongate composite structure less injurious to the urethra, urine bladder, anus, colon or rectum, and reduces the injury of such organs. Furthermore, the soft core of viscoelastic material may be formed to enclose and protect mechanical adjustment components and other components of the composite structure, whereby fibrosis is prevented from growing into such components.

In another alternative to the first embodiment, the elongate composite structure is designed for hydraulic adjustment, such as the hydraulic solutions disclosed in International Application No. WO 01/50833. In this alternative, the base material forms a closed tubing, which can be inflated by adding hydraulic fluid to the interior of the tubing and deflated by withdrawing hydraulic fluid from the interior of the tubing. The coating of Teflon™, Parylene™ or metal may cover the inner surface of the tubing. The base material may form two coaxial tubular layers of hard silicon, and the property improving means may comprise a tubular intermediate layer of a soft viscoelastic material located between the coaxial tubular layers. Alternatively, the base material may form an outer tubular layer and an inner arcuate layer attached to the outer tubular layer, the outer and inner layers defining a curved space extending longitudinally along the tubing. The property improving means may comprise a viscoelastic material filling the space. The tubing is applied around the urethra, urine bladder, anus, colon or rectum so that the space with viscoelastic material is located closest to the urethra, urine bladder, anus, colon or rectum. The viscoelastic material gives the advantages that erosion of the urethra, urine bladder, anus, colon or rectum is reduced and the risk of hydraulic fluid leaking from the tubing is decreased.

In accordance with a second embodiment of the invention, the base material forms a first layer and the property improving means comprises a second layer applied on the first layer, wherein the second layer is more fatigue resistant than the first layer. The first layer preferably is comprised of hard silicone, whereas the second layer preferably is comprised of a polyurethane layer. In a traditional silicone band, especially the tubular type, that is formed in a loop to constrict the urethra, urine bladder, anus, colon or rectum, the inner surface of the band loop that contacts the urethra, urine bladder, anus, colon or rectum forms bulges and creases that repeatedly change as the band is subjected to dynamic movements from the urethra, urine bladder, anus, colon or rectum and when the size of the band is adjusted. As a consequence, the implanted traditional silicone band has the drawback that it may crack after some time due to fatigue of the silicone material. With the elongate composite structure of the invention, in which hard silicone may constitute the base material and a fatigue resistant polyurethane layer covers the silicone material on the side of the elongate composite structure that contacts the urethra, urine bladder, anus, colon or rectum, this drawback is eliminated.

The property improving means suitably comprises a coating that may be coated on the layer of hard silicone and/or the layer of polyurethane, wherein the coating has better aggressive body fluid resistance properties and/or better anti-friction properties-.than hard silicone. As described above in connection with the first embodiment, the coating may comprise a Teflon™ or Parylene™ coating, or a biocompatible metal coating.

The layer of hard silicone may form an inflatable tubing and the layer of polyurethane may cover the hard silicone layer within the tubing.

In accordance with a third embodiment of the invention, the base material forms an inflatable tubing and the property improving means comprises a liquid impermeable coating coated on the base material. The coating may be coated on the external and/or internal surface of the tubing. Preferably, the liquid impermeable coating comprises a Parylene™, i.e., poly-paraxylylene polymer, coating, or a biocompatible metal coating. Where hard silicone, which is a liquid semipermeable material, constitutes the base material, the coating of Parylene™, i.e., poly-paraxylylene polymer, or metal gives the advantage that the tubing may be inflated by hydraulic fluid under pressure without risking fluid diffusing through the silicone wall of the tubing.

Also, in the third embodiment, the base material may form two coaxial tubular layers of hard silicon, and the property improving means may comprise a tubular intermediate layer of a soft viscoelastic material located between the coaxial tubular layers. Alternatively, the base material may form an outer tubular layer of hard silicone and an inner arcuate layer of silicone attached to the outer tubular layer. The outer and inner layers define a curved space extending longitudinally along the tubing and filled with the viscoelastic material. The tubing is intended to be applied around the urethra, urine bladder, anus, colon or rectum so that the space with viscoelastic material is located closest to the urethra, urine bladder, anus, colon or rectum.

In accordance with a fourth embodiment of the invention, the property improving means comprises gas, such as air, contained in a multiplicity of cavities formed in the base material to improve the flexibility of the composite structure. In this case, Teflon™, i.e., PTFE or poly-tetra-flouro-ethylene, advantageously constitutes the base material. The cavities may be defined by net structures of the Teflon™, i.e., PTFE or poly-tetra-flouro-ethylene, material. Thus, the resulting composite structure of Teflon™, i.e., PTFE or poly-tetra-flouro-ethylene, and cavities filled with gas is strong, flexible and aggressive body fluid resistant, and has good tensile strength and good anti-friction properties. Also, in the fourth embodiment, the elongate composite structure may comprise an inflatable tubing.

The present invention also provides an implantable constriction device for treating an incontinent patient, comprising an elongate composite structure adapted to constrict the urethra, urine bladder, anus, colon or rectum of the patient, wherein the composite structure includes an elongate biocompatible self-supporting base material having surfaces exposed to aggressive body cells, when the constriction device is implanted in the patient, and a cell barrier coating on the surfaces to prevent body cells from breaking down the base material, which is typically silicone. If the base material were broken down by such body cells, typically macrophages or killer cells, histological particles would be spread in the human body.

The barrier coating may comprise a Parylene™, i.e., poly-paraxylylene polymer, coating or a biocompatible metal coating.

Alternatively, the barrier coating may comprise a composite of different materials to achieve the cell-barrier protection as described above. There are several examples of such composite materials on the market, for example a composite of polyurethane and silicone called Elaston™.

BRIEF DESCRIPTION OF THE DRAWINGS:

Referring to the drawing figures, like reference numerals designate identical or corresponding elements throughout the several figures.

DETAILED DESCRIPTION OF THE INVENTION

Figure 1:
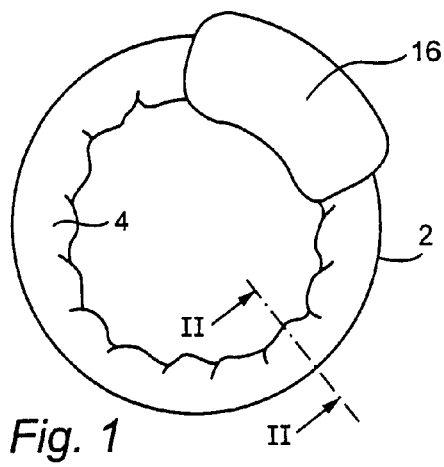
FIG. 1 is a front view of a mechanical constriction device according to the present invention.
Figure 2:
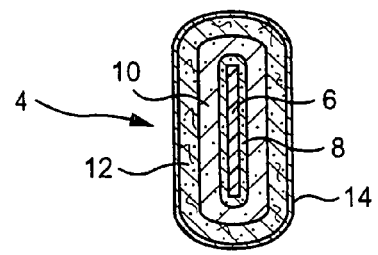
FIG. 2 is an enlarged cross-section along the line II-II in FIG. 1.

FIG. 1 illustrates a mechanical constriction device 2 according to the invention comprising an elongate composite structure 4 adapted to extend around and constrict the urethra, urine bladder, anus, colon or rectum of a patient. Referring to FIG. 2, the elongate composite structure 4 comprises a strong band 6 of nylon or the like, a tubular layer 8 of hard silicone, in which the band 6 slides, a soft layer 10 of a viscoelastic material, here a silicone gel having a hardness not more than 20 Shure, encircling the hard silicone layer 8, and a tubular layer 12 of a self-supporting base material of hard silicone having a hardness of at least 60 Shure, surrounding the soft silicon layer 10. A coating 14 of Teflon™, i.e. PTFE or poly-tetra-flouro-ethylene, Parylene™, i.e., poly-paraxylylene polymer, or a biocompatible metal, such as gold, silver or titanium, is coated on the outer hard silicone layer 12 to make the composite structure resistant to aggressive body fluids and to give the composite structure good anti-friction properties. A coating of Teflon™, i.e. PTFE or poly-tetra-flouro-ethylene, ParyleneTM, i.e., poly-paraxylylene polymer., or metal may also be coated on the internal surface of the inner tubular hard silicone layer 8 to reduce the friction between the nylon band 6 and the layer 8. The constriction device 2 has an adjustment means 16 that can displace the end portions of the nylon band 6 relative to each other to either increase or decrease the constriction of the urethra, urine bladder, anus, colon or rectum.

Figure 3:
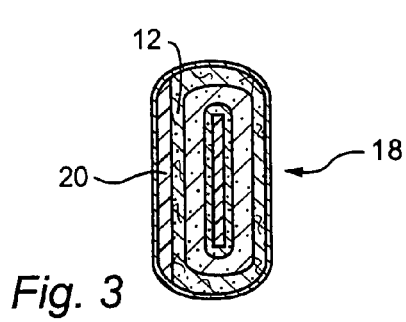
FIGS. 3 and 4 are modifications of the embodiment shown in FIG. 2.

FIG. 3 shows an elongate composite structure 18 similar to that of FIG. 2, except that a layer 20 of a fatigue resistant material, here polyurethane, is applied on the hard silicone layer 12 along the inner side of the structure 18 that is intended to contact the urethra, urine bladder, anus, colon or rectum. Alternatively, the layer 20 may be tubular and surround the layer 12.

Figure 4:
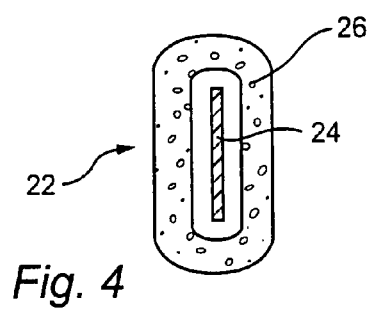

FIG. 4 shows a cross-section of an elongate composite structure 22 of an embodiment of the invention, in which Teflon™, i.e.. PTFE or poly-tetra-flouro-ethylene, constitutes the self-supporting base material, which is formed with a longitudinal cavity in which a strong nylon band 24 slides. Property improving means in the form of a gas, here air, contained in a multiplicity of cavities 26 are formed in the base material to improve the flexibility thereof.

Figure 5:
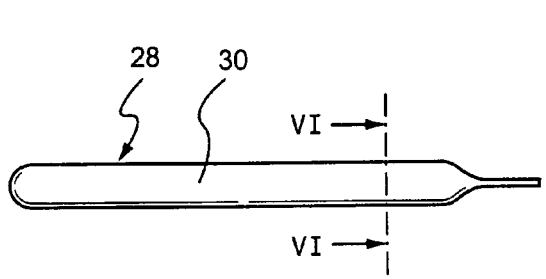
FIG. 5 is a front view of a hydraulic constriction device of the invention.
Figure 6:
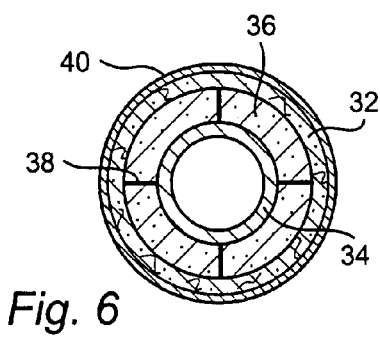
FIG. 6 is an enlarged cross-section along the line VI-VI in FIG. 5.

FIGS. 5 and 6 show a hydraulic constriction device 28 according to the invention comprising an elongate composite structure in the form of an inflatable tubing 30, in which the base material of hard silicone forms an outer tubular layer 32 and an inner coaxial layer 34. A viscoelastic material, here soft silicone gel, forms an intermediate layer 36 located between the tubular layers 32 and 34. Four longitudinal partition walls 38 between the tubular layers 32 and 34 divide the intermediate layer 36 into four sections to prevent the silicone gel from displacing in the circumferential direction of the tubing 30. (Also, the embodiments according to FIGS. 2 and 3 may be provided with such longitudinal partition walls.) The outer layer 32 is coated with a coating 40 of Teflon™, i.e., PTFE or poly-tetra-flouro-ethylene, Parylene™, i.e., poly-paraxylylene polymer., or metal. Also, the inner layer 34 may be coated with a coating of Teflon™, i.e., PTFE or poly-tetra-flouro-ethylene, Parylene™, i.e., poly-paraxylylene polymer, or metal. If a Parylene™, i.e., poly-paraxylylene polymer, or metal coating is chosen the composite structure will be completely liquid impermeable.

Figure 7:
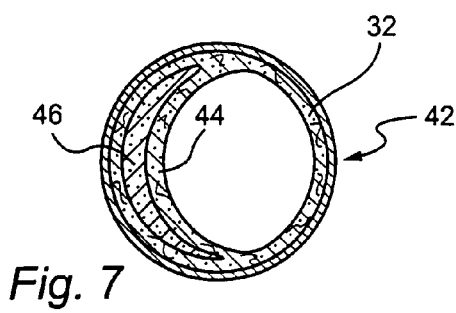
FIGS. 7-10 are modifications of the embodiment shown in FIG. 6.

FIG. 7 shows a tubing 42 similar to that of FIG. 6, except that an inner arcuate layer 44 is substituted for the inner tubular layer 34. The arcuate layer 44 is attached to the outer tubular layer 32, so that the outer tubular layer 32 and the arcuate layer 44 define a curved space extending longitudinally along the tubing 42. A viscoelastic material, here silicone gel 46, fills the space. In this embodiment there is no need for partition walls of the kind shown in the embodiment shown in FIG. 6. The tubing 42 is intended to be applied around the urethra, urine bladder, anus, colon or rectum so that the space with the protecting soft silicone gel 46 is located close to the urethra, urine bladder, anus, colon or rectum.

As taught by the embodiment of FIG. 7, in the composite structures shown in FIGS. 2 and 3, the soft silicone gel may alternatively be applied in a longitudinal space close to the inner side of the elongate composite structure 4 and 18, respectively, that is intended to contact the urethra, urine bladder, anus, colon or rectum.

In the same manner as described above in connection with the embodiment of FIG. 3, a layer of a fatigue resistant material, here polyurethane, may be applied on the outer tubular layer 32 of hard silicone of the tubing 30 and 42, respectively, along the side of the tubing 30 and 42, respectively, that is intended to contact the urethra, urine bladder, anus, colon or rectum, when the tubing 30 and 42, respectively, encircles the urethra, urine bladder, anus, colon or rectum.

Figure 8:
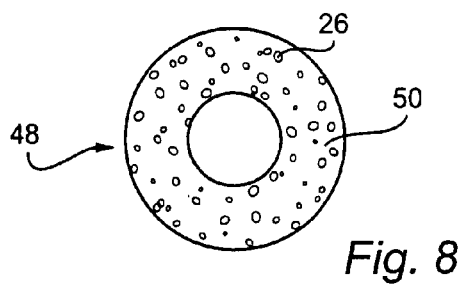

FIG. 8 shows a cross-section of an elongate composite structure 48 of an embodiment of the invention, in which Teflon™, i.e., PTFE or poly-tetra-flouro-ethylene, constitutes the self-supporting base material, which is formed to an inflatable tubing 50. Property improving means in the form of gas contained in a multiplicity of cavities 26 are formed in the base material to improve the flexibility of the tubing 50.

Figure 9:
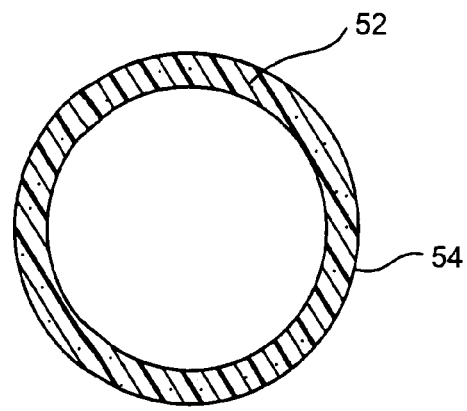

FIG. 9 shows a cross-section of a tubular composite structure of an embodiment of the invention, in which the self-supporting base material 52 is made of a polymer material suited for implantation, for example silicone or polyurethane. A property improving coating 54, for example made of Parylene™, i.e., poly-paraxylylene polymer, Teflon™, i.e., PTFE or poly-tetra-flouro-ethylene, or metal, is applied on the external surface or on both the external and internal surfaces of the tubular structure.

Figure 10:
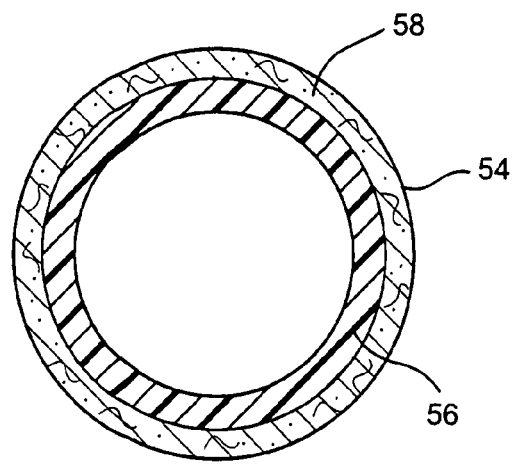

FIG. 10 shows the same embodiment as FIG. 9, except that the base material comprises a layer 56 of polyurethane surrounded by a layer 58 of silicone.

Figure 11:
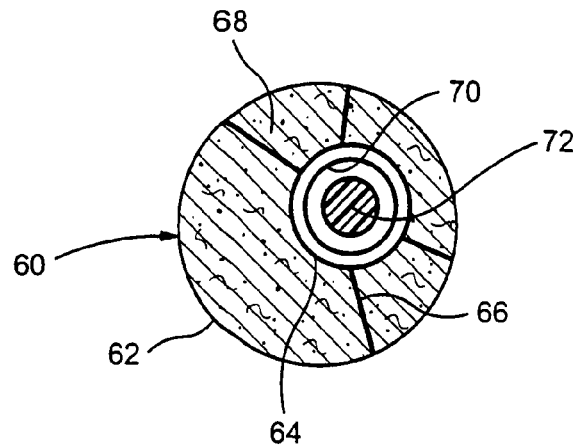
FIG. 11 is a modification of the embodiment shown in FIG. 2.

FIG. 11 shows a cross-section of a mechanical constriction device of another embodiment of the invention, comprising a double walled tubing 60, an external wall 62 and an internal wall 64 spaced from the external wall 62, of a self-supporting base material of hard silicone. The tubing 60 has partition walls 66 dividing the space between the external and internal walls 62 and 64, respectively, of the tubing 60 into longitudinal cells 68, which are filled with a soft viscoelastic material, for example silicone gel. The internal wall 64 is coated with a friction reducing coating 70, for example made of Teflon™ or the like. A strong band 72 of nylon or the like slides in the tubing 60 on the friction reducing coating 70 to enable adjustment of the constriction device in the same manner as described above in connection with the embodiment according to FIGS. 1 and 2.

Although the present invention has been described in terms of particular embodiments, it is not intended that the invention be limited to those embodiments. Modifications of the embodiments within the spirit of the invention will be apparent to those skilled in the art. The scope of the invention is defined by the claims that follow.

What is claimed is:

1. An implantable constriction device for treating an incontinent patient, the device comprising;
   an elongate composite structure adapted to encircle and postoperatively adjustably constrict the urethra, urine bladder, anus, colon or rectum of the incontinent patient for treating the incontinent patient to increase or decrease the constriction of the urethra, urine bladder, anus, colon or rectum, wherein said elongate composite structure is comprised of a base material making said composite structure self-supporting and property improving means for improving at least one physical property of said composite structure other than self-supporting properties,
   the base material comprising a layer of silicone,
   the property improving means comprising a layer f polyurethane, wherein the layer of silicone surrounds the layer of polyurethane, and wherein at least one of the layer of silicone and the layer of polyurethane comprises a poly-para-xylylene polymer coating.

2. The implantable constriction device according to claim 1, wherein the silicone constituting said base material is a hard silicone.

3. The implantable constriction device according to claim 1, wherein said base material forms an inflatable tubing.

4. The implantable constriction device according to claim 3, wherein said tubing has an inner surface defining an interior of said tubing, and said coating covers said inner surface.

5. The implantable constriction device according to claim 1, wherein said property improving means is more fatigue resistant than said base material.

6. The implantable constriction device according to claim 5, wherein said property improving means comprises a coating coated cm said base material, said coating having better aggressive body fluid resistance properties and/or better anti-friction properties than said base material.

7. The implantable constriction device according to claim 3, wherein said tubing has an external surface of said base material and an internal surface of said base material defining the interior of said tubing, said coating being coated on said external surface and/or internal surface.

8. An implantable constriction device for treating an incontinent patient, the device comprising:
   an elongate composite structure adapted to adjustably constrict the urethra, urine bladder, anus, colon or rectum of the patient, said elongate composite structure being comprised of a base material making said composite structure self-supporting and property improving means for improving at least one physical property of said composite structure other than self-supporting properties,
   the base material comprising a layer of polyurethane and a layer of silicone,
   the property improving means comprising a layer or coating applied on the base material, the layer or coating applied on the base material being of a material different from the base material, and being at least along a side of said elongate composite structure that is intended to contact the urethra, urine bladder, anus, colon or rectum,
   wherein said property improving means comprises a core of a viscoelastic material covered with said self-supporting base material, and said property improving means further comprises a poly-para-xylylene polymer, poly-tetra-fluoro-ethylene, or a biocompatible metal coating.

9. The implantable constriction device according to claim 8, wherein said viscoelastic material is selected from the group consisting of silicone gel, cellulose gel, and collagen gel.

10. The implantable constriction device according to claim 8, wherein said base material forms an outer tubular layer and an inner arcuate layer attached to said outer tubular layer, said outer and inner layers defining a curved space extending longitudinally along said tubing, and said property improving means comprises viscoelastic material filling said space.

11. The implantable constriction device according to claim 8, wherein said base material forms two coaxial tubular layers and said property improving means comprises a tubular intermediate layer comprising the core of viscoelastic material located between said coaxial tubular layers.

12. The implantable constriction device according to claim 8, wherein the biocompatible metal coating is gold, silver or titanium.

* * * * *